(12) United States Patent
Willner et al.

(10) Patent No.: US 7,018,518 B2
(45) Date of Patent: Mar. 28, 2006

(54) BIOSENSOR CARRYING REDOX ENZYMES

(75) Inventors: Itamar Willner, Mevasseret Zion (IL); Eugenii Katz, Jerusalem (IL); Maya Zayats, Jerusalem (IL)

(73) Assignee: Yissum Research Development Company of The Hebrew University of Jerusalem, Jerusalem (IL)

(*) Notice: Subject to any disclaimer, the term of this patent is extended or adjusted under 35 U.S.C. 154(b) by 565 days.

(21) Appl. No.: 10/133,635

(22) Filed: Apr. 29, 2002

(65) Prior Publication Data

US 2003/0148169 A1    Aug. 7, 2003

Related U.S. Application Data

(60) Provisional application No. 60/353,193, filed on Feb. 4, 2002.

(51) Int. Cl.
  *G01N 27/327*    (2006.01)
  *H01M 8/16*    (2006.01)
(52) U.S. Cl. ............... 204/403.14; 204/403.01; 429/2; 427/2.12
(58) Field of Classification Search ........... 204/403.01, 204/403.14; 205/777.5, 778, 792; 429/2, 429/43, 213; 427/2.12
  See application file for complete search history.

(56) References Cited

U.S. PATENT DOCUMENTS 6,241,863 B1 * 6/2001 Monbouquette ......... 205/777.5

OTHER PUBLICATIONS

Habermuller et al. "Electron-Transfer Mechanisms in Amperometric Biosensors", *Anal. Chem.*, 366:560-568, 2000.
Heller, "Electrical Wiring of Redox Enzymes", *Acc. Chem. Res.*, 23:128-134, 1990.
Willner et al. "Electrical Contact of Redox Enzyme Layers Associated with Electrodes: Routes to Amperometric Biosensors", *Electroanalysis*, 9 (13):965-977, 1997.
Chen et al., "A Miniature Biofuel Cell", *J. Am. Chem. Soc.*, 123:8630-8631, 2001.
Katz et al., "Short Communication: A Non-Compartmentalized Glucose | $O_2$ Biofuel Cell by Bioengineered Electrode Surfaces", *J. Electroanal. Chem.*, 479:64-68, 1999.
Willner et al., "Integration of a Reconstituted de Novo Synthesized Hemoprotein and Native Metalloproteins with Electrode Supports for Bioelectronic and Bioelectrocatalytic Applications", *J. am. Chem. Soc.*, 121:6455-6468, 1999.

(Continued)

*Primary Examiner*—Kaj K. Olsen
(74) *Attorney, Agent, or Firm*—Browdy and Neimark, PLLC

(57) ABSTRACT

The present invention concerns an electrode carrying immobilized redox enzymes such that electric charge can flow between an electron mediator group to the enzyme cofactor by the use of boronic acid or a boronic acid derivative that acts as a linker moiety between the cofactor and the electron mediator group. The invention also concerns devices and systems that make use of the electrode of the invention, such as bio-sensors and fuel cells, the electrode being one of the components thereof.

19 Claims, 7 Drawing Sheets

OTHER PUBLICATIONS

Willner et al., "Mediated Electron Transfer in Glutathione Reductase Organized in Self-Assembled Monolayers on Au-Electrodes", *J. Am. Chem. Soc.*, 114:10965-10966, 1992.

Willner et al., "Development of Novel Biosensor Enzyme Electrodes: Glucose Oxidase Multilayer Arrays Immobilized onto Self-Assembled Monolayers on Electrodes", *Adv. Mater.*, 5 (12):912-915, 1993.

Gregg et al., "Redox Polymer Films Containing Enzymes. 1. A Redox-Conducting Epoxy Cement: Synthesis, Characterization, and Electrocatalytic Oxidation of Hydroquinone", *J. Phys. Chem.*, 95:5970-5975, 1991.

Cosnier et al., "Amperometric Detection of Nitrate via a Nitrate Reductase Immobilized and Electrically Wired at the Electrode Surface", *Anal. Chem.*, 66:3198-3201, 1994.

Badia, et al., "Intramolecular Electron-Transfer Rates in Ferrocene-Derivatized Glucose Oxidase", *J. Am. Chem. Soc.*, 115 (16):7053-7060, 1993.

Katz et al., "Glucose Oxidase Electrodes via Reconstruction of the Apo-Enzyme: Tailoring of Novel Glucose Biosensors", *Anal. Chim. Acta*, 385:45-58, 1999.

Buckmann et al., "Synthesis of $N^6$-(2-Aminoethyl)-FAD, $N^6$-(6-Carboxyhexyl)-FAD, and Related Compounds", in McCormick, D.B. (Ed.), *Methods in Enzymology: Vitamins and Coenzymes, Academic Press*, 280(1):360, 1997.

James et al., "Saccharide Sensing with Molecular Receptors Based on Boronic Acid", *Angew. Chem. Int. Ed. Engl.*, 35:1911-1922, 1996.

Lorand et al., "Polyol Complexes and Structure of the Benzeneboronate Ion", *J. Org. Chem.* 24, 769-88, 1959.

Katz et al., "Kinetic Separation of Amperometric Responses of Composite Redox-Active Monolayers Assembled onto Au Electrodes: Implications to the Monolayers' Structure and Composition", *Langmuir* 13: 3364-3373, 1997.

Allvarez-Icazan et al, "Observation of Direct Electron Transfer from the Active Center of Glucose Oxidase to a Graphite Electrode Achieved Through the Use of Mild Immobilization", Biochemistry and Bioenergetics, vol. 33, 1994, pp. 191-199.

Frew, J.E., and H.A.O. Hill, "Electron-Transfer Biosensors", Phil. Trans. R. Soc. Lond., vol. B316, 1987, pp. 95-106.

Narasimhan, Krishna, and Lemuel B. Wingard, Jr., "Enhanced Direct Electron Transport with Glucose Oxidase Immobililzed on (Aminophenyl)boronic Acid Modified Glassy Carbon Electrode", Anal. Chem., vol. 58, 1986. pp. 2984-2987.

Willner et al, "Electrical Wiring of Glucose Oxidase by Reconstitution of FAD-Modified Monolayers Assembled onto Au-Electrodes", J. Am. Chem. Soc., vol. 118, 1996, pp. 10321-10322.

Zayats et al, "Electrical Contacting of Flavoenzymes and $NAD(P)^=$-Dependent Enzymes by Reconstitution and Affinity Interactions on Phenylboronic Acid Monolayers Associated with Au-Electrodes", J. Am. Chem. Soc., vol. 124, 2002, pp. 14724-14735.

Zayats et al, "Electrical Contacting of Glucose Oxidase by Surface-Reconstitution of the Apo-Protein on a Relay-Boronic Acid-FAD Cofactor Monolayer".

* cited by examiner

BIOSENSOR CARRYING REDOX ENZYMES

This application claims the benefit of U.S. Provisional Application 60/353,193 filed on Feb. 4, 2002.

FIELD OF THE INVENTION

The present invention is generally in the field of bioelectronlics and concerns electrically conducting solid matrices (to be referred to herein as "electrodes") carrying redox enzymes such that an electric charge can flow between the surface of the electrode and the enzymes rendering them catalytically active. Also provided by the invention is a process for the preparation of the electrodes as well as devices, systems and methods making use of such electrodes.

RELATED PRIOR ART

The art believed to be relevant as a background to the present invention consists of the following:
1. Habermuller, L., Mosbach, M., Schuhmann, W., Fresenius J.; *Anal. Chem.*, 366:560–568, 2000.
2. Heller, A., *Acc. Chem. Res.*, 23:128–134, 1990.
3. Willner, I., Katz, E., Willner B., *Electroanalysis*, 9:965–977, 1997.
4. Chen, T., Barton, S. C., Binyamin, G., Gao, Z. Q., Zhang, Y. C., Kim H. H., Heller, A., *J. Am. Chem. Soc.*, 123: 8630–8631, 2001.
5. Katz, E., Willner, I., Kotlyar, A. B., *J. Electroanal. Chem.*, 479:64–68, 1999.
6. Willner, I., Heleg-Shabtai, V., Katz, E., Rau, H. K., Haehnel, W., *I. am. Chem. Soc.*, 121:6455–6468, 1999.
7. Willner, I., Katz, E., Riklin, A., Kahser, R., *J. Am. Chem. Soc.*, 114:10965–10966, 1992.
8. Willner, I., Riklin, A., Shoham B., Rivenzon, D., Katz, F., *Adv. Mater.*, 5:912–915, 1993.
9. Gregg, A. A., Heller, A., *J. Phys. Chem.*, 95:5970–5975, 1991.
10. Cosnier, S., Innocent, C., Jouanneau, Y., *Anal. Chem.*, 66:3198–3201, 1994.
11. Badia, A., Carlini, R., Fernandez, A., Battaglini, F., Mikkelsen, S. R., English, A. M., *J. Am. Chem. Soc.*, 115:7053–7060, 1993.
12. Willner, I., Heleg-Shabtai, V., Blonder, R., Katz, E., Tao, G., Buckmann, A. F., Heller, A., *J. Am. Chem. Soc.*, 118:10321–10322, 1996.
13. WO 97/45720
14. Katz, E., Riklin, A., Heleg-Shabtai, V., Willner, I., Buckmann, A. F., *Anal. Chim. Acta*, 385:45–58, 1999.
15. Buckmann, A. F., Wray, V., Stocker, A., in McCormick, D. B. (Ed.), *Methods in Enzymology: Vitamins and Coenzymes*, Academic Press, 280(1):360, 1997.
16. James, T. D., Sandanayake, K., Shinkai, S., *Angew. Chem. Int. Ed. Engl.*, 35:1911–1922, 1996.
17. Lorand, J. P., Edwards, J. O., J. Org. Chem. 24, 76–88, 1959.
18. Katz, E, Willner, I., *Langmuir* 13: 3364–3373, 1997.

The references from the above list will be acknowledged by indicating their numbers from the list.

BACKGROUND OF THE INVENTION

Electrically contacting redox-enzymes to electrodes is a major goal for developing amperometric biosensers,[1-3] biofuel cells[4-5] and bioelectronic elements.[6] Integrated electrically-contacted enzyme-electrodes were prepared by the tethering of an electron mediator group to the enzyme associated with the electrode,[7-8] and by the immobilization of redox-enzymes in redox-active polymers assembled on electrodes.[9-10] The effectiveness of electron transfer communication in these systems is, however, substantially lower than the electron transfer turnover rates of the enzymes with their native substrates.[11] This has been attributed to a random, non-optimal, modification of the redox-proteins by the electroactive relay units, and to the random orientation of the enzymes in respect to the electrode support.[3] It was previously demonstrated[12-14] that the reconstitution of an apo-flavoenzyme, apo-glucose oxidase (Apo-GOx), on a relay-FAD (flavin adenine dinucleotide) monolayer associated with an electrode yields an aligned, electrically contracted, enzyme-electrode with an unprecedented effective electron transfer communication that is similar to the electron transfer turnover rate of the enzyme with its native substrate (oxygen). This efficient electrical communication between the surface reconstituted bioelectrocatalyst and the electrode was utilized to develop enzyme-electrodes for a glucose sensor,[12-14] and for a glucose-base biofuel cell.[5] To generate the relay-FAD monolayer in these systems, the covalent coupling of a synthetic aminoethyl-FAD unit to the relay component is a key step. The elaborate synthesis of this cofactor[15] turned the approach to be of limited practical utility.

SUMMARY OF THE INVENTION

According to the invention the problem of coupling of an electron mediator group to an enzyme cofactor has been solved by the use of boronic acid or a boronic acid derivative as a linker moiety between the cofactor and an electron mediator group. Boronic acid is an active ligand for the association of cis-diols, and particularly cis-diols being part of cyclic saccharides[16]. In accordance with the invention, boronic acid or a boronic acid derivative is used to bind to two cis-hydroxyl groups of the cofactor and to the electron mediator group.

In accordance with the invention, there is provided an electrode carrying immobilized groups having the general formula:

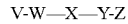

wherein
V is a binding moiety that can chemically associate with, attach to, or chemically sorb onto the electrode;
W is an electron mediator group that can transfer electrons between the electrode and Y;
X is a linker moiety;
Y is a cofactor of a redox enzyme having, when not bound to X at least one pair of cis hydroxyl groups; and
Z is a redox enzyme;

characterized in that X is a boronic acid derivative.

In accordance with a preferred embodiment, X has the formula

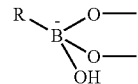

wherein R is an aliphatic or aromatic moiety, e.g. phenyl, naphthyl or alkyl, optionally substituted by at least one carboxy, carbonyl, amino, hydroxy or thio group.

In accordance with a specific embodiment; X is an aminophenyl boronic acid derivative.

Typical cofactors are FAD, NAD$^+$ and NADP$^+$. Examples of enzymes are glucose oxydase, lactate hydrogenase and malic enzyme.

The invention also relates to a process for preparing the electrodes, having features as outlined below with reference to the below-described specific embodiment. In particular, the invention provides a process for preparing an electrode carrying immobilized redox enzymes Z comprising:
  (i) forming a layer on the surface of the electrode comprising groups of the formula V-W—X—Y, wherein V is a binding moiety that can chemically associate with, attach to, or chemically sorb onto the electrode and W is an electron mediator group that can transfer electrons between the electrode and Y, Y being a cofactor of the enzyme and X is a linker group;
  (ii) contacting said electrode with one or more enzyme molecule, devoid of a cofactor to complex said enzymes with said cofactor to yield a immobilized groups V-W—X—Y-Z, wherein Z is a catalytically functional enzyme that can catalyze a redox reaction; said method being characterized in that said cofactor has at least one pair of cis hydroxyl groups and said process comprises binding said cofactor to said electron mediator group by a group X being a boronic acid derivative.

According to a specific embodiment, the process comprises forming a layer of groups V-W, then binding Y thereto through the intermediary of X followed by reconstitution of the enzyme on the electrode to eventually yield immobilized groups V-W—X—Y-Z, with the enzyme Z being catalytically active in catalyzing a redox reaction. The process according to this embodiment comprises:
  (i) forming a layer on the surface of the electrode comprising groups of the formula V-W, wherein V is a binding moiety that can chemically associate with, attach to, or chemically sorb onto the electrode and W is an electron mediator group that can transfer electrons between the electrode and a cofactor Y of the enzyme;
  (ii) binding Y to said groups; and
  (iii) contacting said electrode with one or more enzyme molecule, devoid of a cofactor to complex said enzymes with said cofactor to yield functional enzymes that can catalyze a redox reaction; said method being characterized in that said cofactor has at least one pair of cis hydroxyl groups and said process comprises binding said cofactor to said electron mediator group by a group X being a boronic acid derivative.

According to one specific embodiment, (b) in the above process comprises binding a boronic acid or a boronic acid derivative to groups V-W immobilized on the electrode to yield immobilized groups V-W—R—B—(OH)$_2$ and then binding Y to the immobilized groups V-W—R—B—(OH)$_2$ to yield immobilized groups V-W—R—B$^-$(OH)—Y.

According to another embodiment, (b) comprises binding a group of the formula R—B—(OH)$_2$ to Y to yield a first binding product R—B$^-$(OH)—Y and then binding said first binding product to immobilized groups V-W to yield immobilized groups V-W—R—B$^-$(OH)—Y.

The invention also concerns devices and systems that make use of the electrode of the invention, such as bio-sensors and fuel cells, the electrode being one of the components thereof. For example, a bio-sensor system or other device making use of the electrode of the invention may be useful for detection of an agent that is a substrate of the redox enzyme. The agent may also be detected in situ or ex vivo, e.g by placing the bio-sensor through catheter into a blood vessel, etc.

As may be appreciated, devices and systems that make use of the electrode also comprise other components such as a reference electrode, the relevant electric/electronic circuitry, etc. For example, in the case of the bio-sensor of the invention, this device/system typically includes also a module connected to the electrode for energizing the electrode and for detecting the response.

A fuel cell making use of the electrode of the invention may be energized by the redox reaction carried out by the enzyme attached to the electrode. Thus, such a fuel cell will comprise also a medium, typically an aqueous medium, that includes a substrate for the enzyme. As a consequence of the result redox reaction, the electrode will be electrically energized.

The electrode according to the invention may be made of or coated by an electrically conducting substance, such as gold, platinum, silver, conducting glass such as indium tin oxide (ITO) with functionalized alkoxysilane on the external surface (silanization of an ITO electrode may, for example, be by refluxing the electrode in an argon atmosphere with 3-aminopropyltriethoxysilane in dry toluene and then drying in an oven).

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF SPECIFIC EMBODIMENTS

Figure 1:
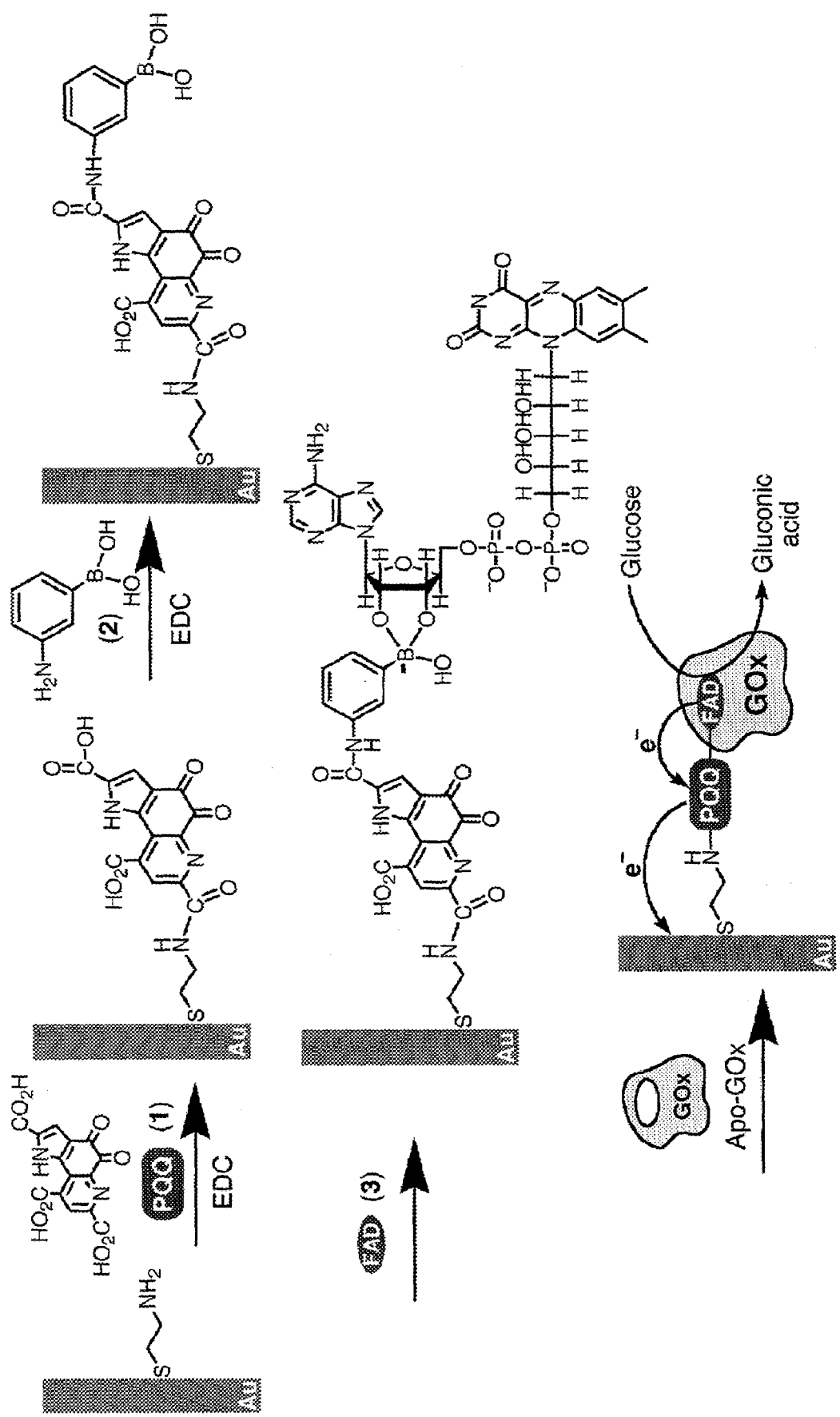
FIG. 1 illustrates the assembly of the reconstituted GOx-electrode and the bioelectrocatalytic oxidation of glucose on this electrode.

Boronic acid is an active ligand for the association of cis-diols, and particularly cis-diols which are a part of cyclic saccharides.[16] The FAD monolayer, according to the present invention, is assembled on an electrode, for example an Au-electrode as outlined in FIG. 1. At fist, pyrroloquinoline quinone, PQQ, (1), is covalently-linked to a cystamine monolayer assembled on the electrode. To the resulting monolayer, 3-aminophenylboronic acid, (2), $1\times10^{-3}$ M, is covalently linked, using 1-ethyl-3-(3-dimethylamino-propyl)-carbodiimide (EDC), $5\times10^{-3}$ M, as a coupling reagent in 0.1 M HEPES-buffer, pH=7.3. The resulting electrode is treated with $1\times10^{-3}$ M FAD, (3), to yield the boronic acid-FAD complex on the monolayer assembly.

Figure 2A:
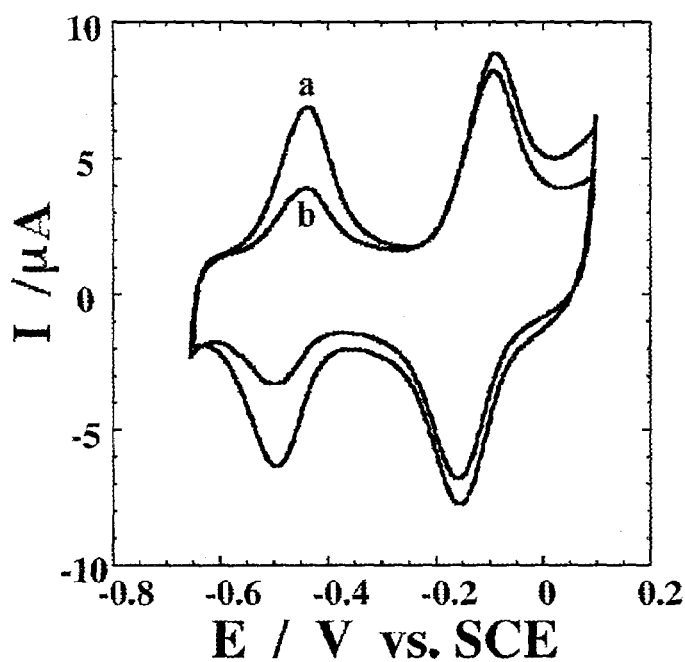
FIG. 2A shows a cyclic voltanunogram of the PQQ-FAD-functionalized Au-electrode at a potential scan rate 200 mV sec$^{-1}$: (a) before reconstitution, (b) after reconstitution with GOx.

FIG. 2A curve (a), shows the cyclic voltammogram of the resulting monolayer composed of PQQ-FAD. The two redox-waves correspond to the quasi-reversible response of the FAD (E°=−0.50 V vs. SCE) and the PQQ (E°=−0.13 V) units, pH=7.0, respectively. Coulometric assay of the redox waves of the electroactive units indicates that the surface coverage of the PQQ and FAD units is $1.8\times10^{-10}$ mole·cm$^{-2}$ and $1.6\times10^{-10}$ mole·cm$^{-2}$, respectively (PQQ:FAD molar ratio is ca. 1:0.9). Treatment of the PQQ-boronic acid derivative-FAD functionalized electrode with apo-GOx results in the surface reconstitution of the protein on the functionalized electrode, FIG. 2A, curve (b).

Figure 2B:
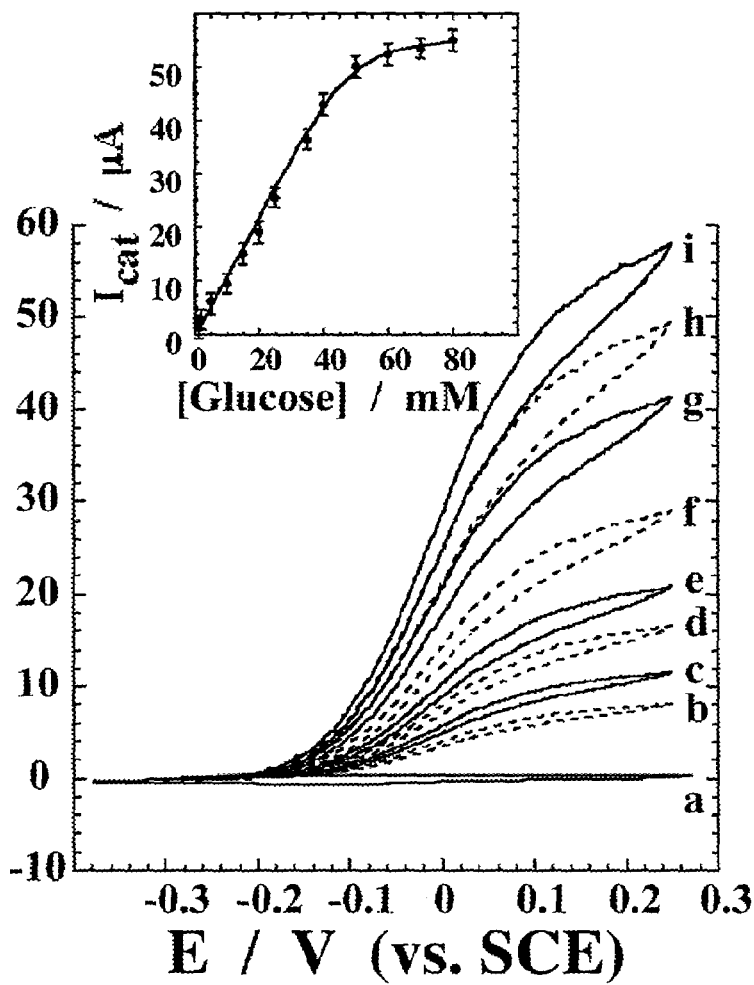
FIG. 2B shows cyclic voltammograms of the GOx-reconstituted on the PQQ-FAD-functionalized Au-electrode (geometrical area 0.3 cm$^2$, roughness factor ca. 1.3) in the presence of different concentrations of glucose: (a) 0 mM, (b) 5 mM, (c) 10 mM, (d) 15 mM, (e) 20 mM, (f) 25 mM, (g) 35 mM, (h) 40 mM, (i) 50 mM; potential scan rate, 2 mV·s$^{-1}$. Data were recorded in 0.1 M phosphate buffer, pH 7.0, under Ar. Inset: Calibration plot of the electrocatalytic currents (E=0.2 V vs. SCE) at variable glucose concentrations.

Microgravimetric quartz-crystal-microbalance measurements following the reconstitution of apo-GOx on a Au/quartz piezoelectric crystal (AT-cut, 9 MHz) modified with the PQQ-FAD monolayer, indicate a surface coverage of the enzyme that corresponds to $2\times10^{-12}$ mole·cm$^{-2}$, thus showing a densely packed monolayer. FIG. 2B shows the cyclic voltammograms of the resulting surface-reconstituted enzyme-electrode in the presence of variable concentrations of glucose. An electrocatalytic anodic current is observed in the presence of glucose implying that the surface-reconstituted enzyme is electrically contacted with the electrode, and that the enzyme is bioelectrocatalytically active towards the oxidation of glucose. The electrocatalytic anodic current is observed at the redox potential of the PQQ units indicating that PQQ mediates the oxidation of the FADH$_2$ formed upon the oxidation of glucose.

FIG. 2B, inset, shows the derived calibration curve corresponding to the currents transduced by the enzyme-electrode system of FIG. 1, at different concentrations of glucose. The current response saturates at glucose concentrations higher than 60 mM. The saturated current value corresponds to the highest turnover-rate of the biocatalyst. From the known surface coverage of the enzyme, and knowing the saturation value of the current density ($i_{max}$=140 μA·cm$^{-2}$), we estimate the electron transfer turnover-rate to be ca. 700 s$^{-1}$ at 25° C. This value is similar[17] to the electron transfer turnover-rate of glucose oxidase with O$_2$, its native substrate.

The efficient electron transfer turnover-rate of the reconstituted enzyme has important consequences on the properties of the enzyme electrode. The amperometric response of the enzyme-electrode in the presence of glucose is not interfered by oxygen. Similarly, the amperometric responses of the electrode (E=0.0 V vs. SCE) in the presence of glucose is unaffected by 20 mM of ascorbic acid or 20 mM of uric acid, common interferants to glucose sensing electrodes. That is, the non-specific oxidation of the interferants has small effect (<5%) on the currents originating from the glucose oxidation.

Figure 3:
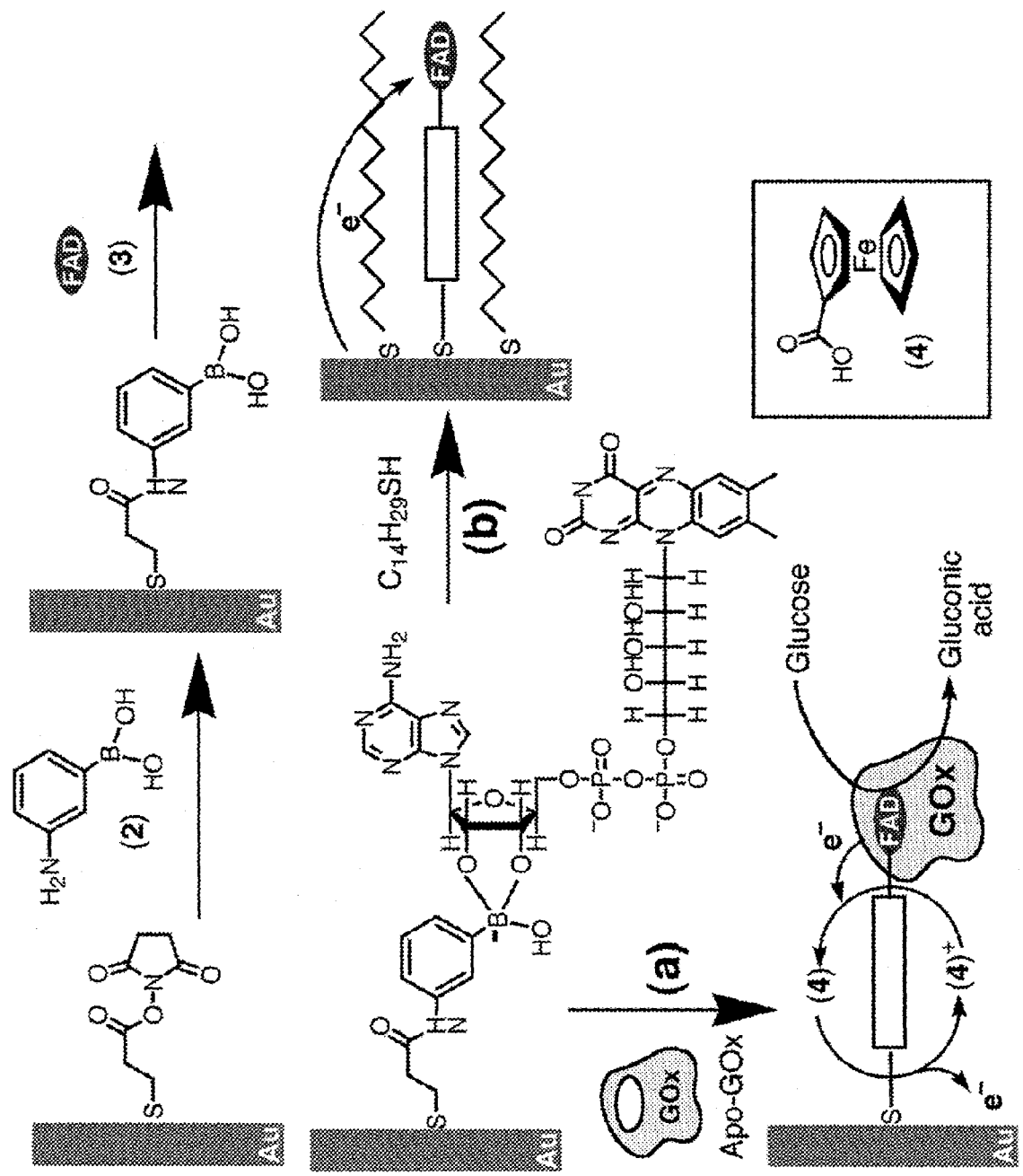
FIG. 3 shows a scheme of a comparative experiment wherein the boronic acid linker group was bound directly to the electrode without an intermediate PQQ group: (a) reconstitution of a non-rigidified FAD-monolayer with GOx and the biocatalytic oxidation of glucose by the enzyme-electrode in the presence of ferrocene carboxylic acid (4) as a diffusional mediator; (b) assembly of a rigidified FAD-monolayer and its chronoamperometric reduction.

In a comparative experiment outlined in FIG. 3, 3-aminophenylboronic acid, (2), was directly linked to a cysteic acid monolayer assembled on the Au-electrode. The cofactor FAD was then linked to the boronic acid ligand, and apo-GOx was reconstituted onto the monolayer. The resulting surface-reconstituted enzyme-electrode lacks direct electrical communication with the electrode, although the enzyme is reconstituted in a biologically-active configuration that is evident by the bioelectrocatalyzed oxidation of glucose in the presence of ferrocene carboxylic acid, (4), as diffusional electron mediator. This control experiment clearly reveals that the PQQ units mediate the electron transport between the FAD redox-site and the electrode surface in the integrated system showed schematically in FIG. 1.

The FAD cofactor includes the diol functionalities of the ribose unit and of the linear glycerol unit. Previous studies[17] indicated that the association constant of the saccharide unit to the boronic acid ligand is substantially higher than that of the linear polyol. A single binding mode of the FAD-cofactor to the boronic acid ligand has been confirmed by chronoamperometric experiments. The 3-aminophenylboronic acid component was covalently linked to the thiolated cysteic acid monolayer associated with the Au-electrode, and the monolayer was interacted with FAD to yield the boronate complex. The resulting monolayer was rigidified with $C_{14}H_{29}SH$, in ethanol solution (1 mM, 2 h) (FIG. 3(b)). It was previously demonstrated[18] that the interfacial electron transfer rate constants to electroactive units in monolayer configurations are sensitive to their spatial separation from the electrode and to the mode of binding. The association of FAD to the boronic acid ligand by the two possible modes would yield a chronoamperometric transient with a biexponential kinetics that correspond to the electron transfer rate constants to the two modes of binding of the FAD units.

Figure 4:
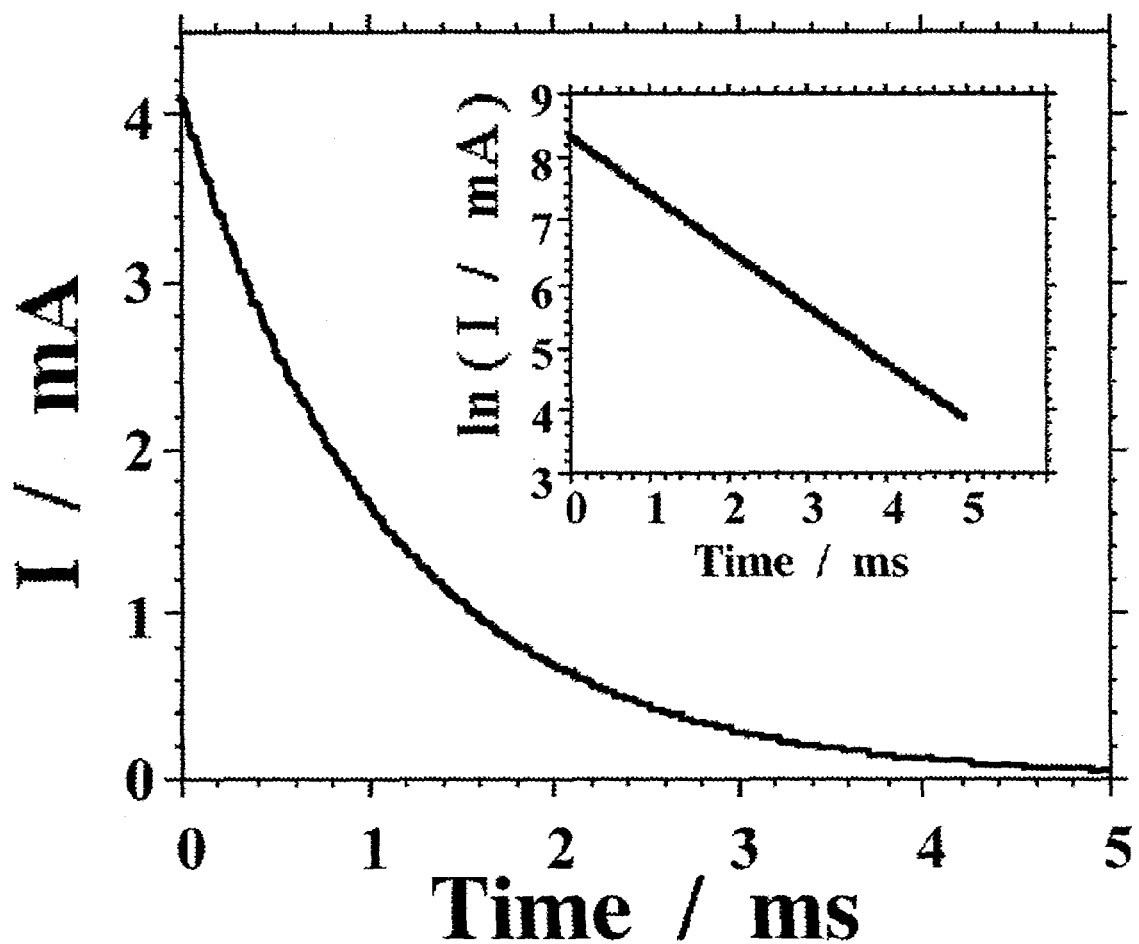
FIG. 4 is a graph showing chronoamperometric current transient corresponding to the reduction of the rigidified FAD-monolayer upon the application of potential step from −0.4 V to −0.6 V. Inset: Semilogarithiic plot of the chronoamperometric transient. The data were recorded in 0.1 M phosphate buffer, pH 7.0, under Ar.

FIG. 4 shows the chronoamperometric transient corresponding to the reduction of the FAD unit. The current transient that follows a single exponential decay, (FIG. 4, inset) suggests a single mode of association of the FAD unit.

Specific examples of cofactors, are the natural FAD and NAD(P)$^+$ cofactors that have cis-hydroxyl groups in the molecules. These hydroxyl groups are used, in accordance with the invention, to covalently bind the cofactors by the use of boronic acid or a boronic acid derivative such as aminophenylboronic acid that specifically binds to the cis-hydroxyl groups, to the modified electrode. Following further reconstitution of enzymes that function with the respective cofactor, the immobilized enzyme-including structures on the electrodes is obtained.

The FAD-cofactor, used in accordance with one embodiment of the invention, inserts itself deeply within the enzyme molecule upon the reconstitution process, thus providing strong (but still non-covalent) binding of the enzyme molecule to the electrode.

The $NAD(P)^+$ (i.e. $NAD^+$ or $NADP^+$) cofactors do not penetrate inside the respective enzymes and provide only weak temporary binding of the enzymes at the electrodes. In order to stabilize the temporary affinity complex with the enzymes, the associated enzyme molecules are preferably cross-linked after they complex with the cofactor-monolayer on the electrode surface, using a bifunctional cross-linker, e.g. glutaric dialdehyde, capable to react with amino groups.

Non-limiting examples of biocatalytic electrodes according to the present invention are composed of: (a) a gold electrode, (b) a cystamine monolayer providing amino groups for the binding of the first redox component of the system, (c) a PQQ monolayer that is the first redox component in the system providing electron transfer from the cofactor to the electrode, (d) aminophenylboronic acid that specifically links between carboxylic groups provided by PQQ and cis-hydroxylic groups provided by the cofactor, (e) a cofactor (FAD, $NAD^+$ or $NADP^+$) monolayer providing attachment and biocatalytic operation of the respective enzymes, (f) the enzyme reconstituted on the cofactor monolayer. In the case of FAD and glucose oxidase the interaction is strong enough by itself, but in the case of $NAD^+$ and malic enzyme or $NADP^+$ and lactate dehydrogenase the interactions are not sufficiently strong and further cross-linking is applied to stabilize the enzyme complex with the $NAD(P)^+$ cofactor monolayer.

Figure 5:
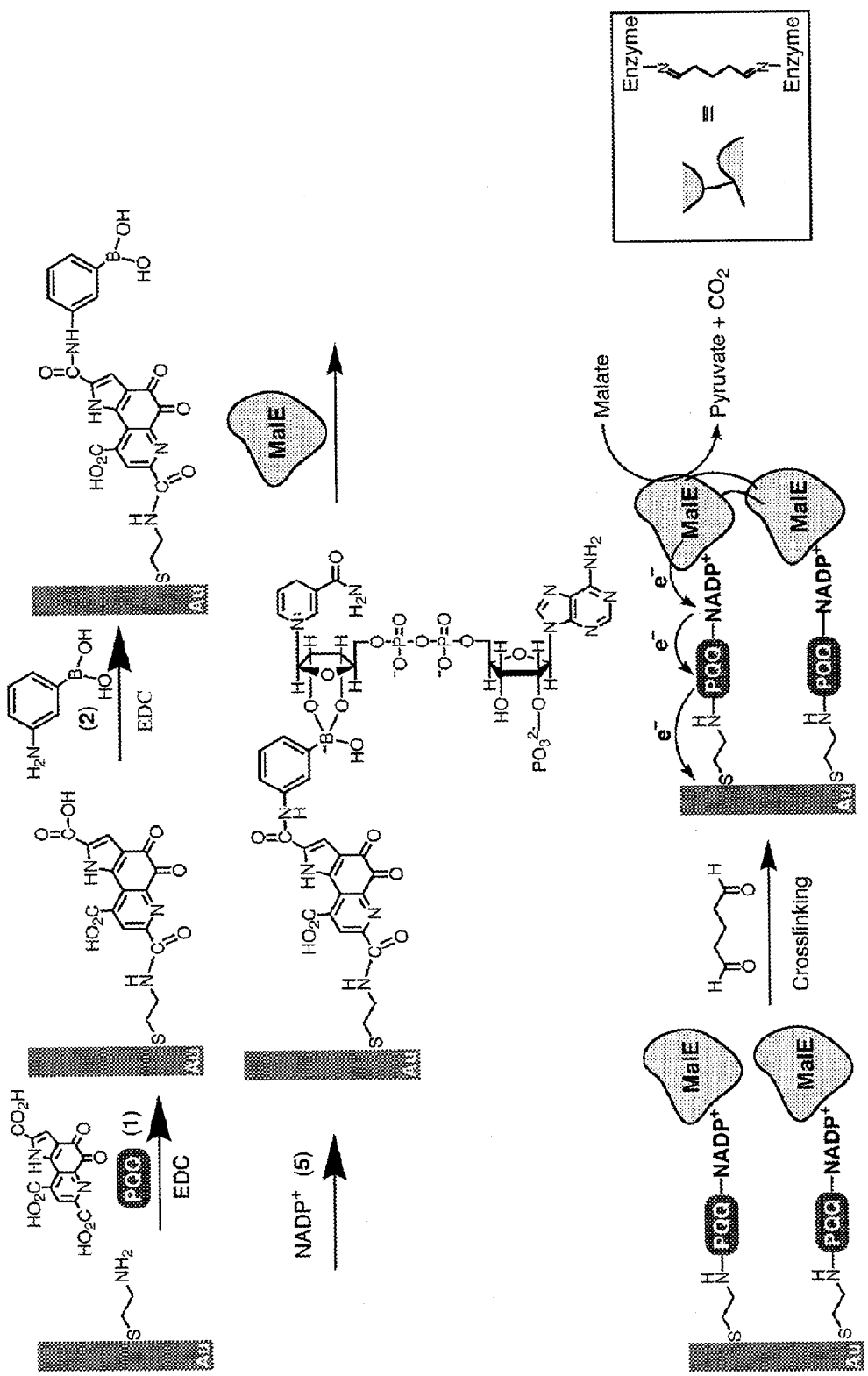
FIG. 5 illustrates the assembly of the reconstituted malic enzyme-electrode and the bioelectrocatalytic oxidation of malate at this electrode.

The assembly of the system composed of cystamine/PQQ/aminophenylboronic acid/$NADP^+$/malic enzyme is schematically showed in FIG. 5 with the following changes, as compared to the cystamine/PQQ/aminophenylboronic acid/FAD/glucose oxidase showed in FIG. 1: (a) $NADP^+$ is used for coupling with the aminophenylboronic acid instead of FAD; (b) Malic enzyme, 1 g mL$^{-1}$, was deposited onto the $NADP^+$ functionalized electrode for 10 minutes and the resulting enzyme layer was cross-linked in a solution of glutaric dialdehyde, 10% (v/v), for 10 minutes; then the electrode was washed with 0.1 M phosphate buffer, pH 7.0.

The system composed of cystamine/PQQ/aminophenylboronic acid/$NAD^+$/lactate dehydrogenase is assembled in a similar way (FIG. 6) with the following changes: (a) $NAD^+$ was used for the coupling with aminophenylboronic acid. (b) Lactate dehydrogenase, 1 g mL$^{-1}$, was deposited onto the $NAD^+$ functionalized electrode for 10 minutes and the resulting enzyme layer was cross-linked in the solution of glutaric dialdehyde, 10% (v/v), for 10 minutes; then the electrode was washed with 0.1 M phosphate buffer, pH 7.0. It should be noted that FAD and $NADP^+$ cofactors have only one pair of cis-hydroxyl groups in the molecules, thus, they have only one possible mode of binding to aminophenylboronic acid. However, $NAD^+$ cofactor has two pairs of cis-hydroxyl groups, that can provide two different modes of the binding, as showed in see FIG. 6.

Figure 7:
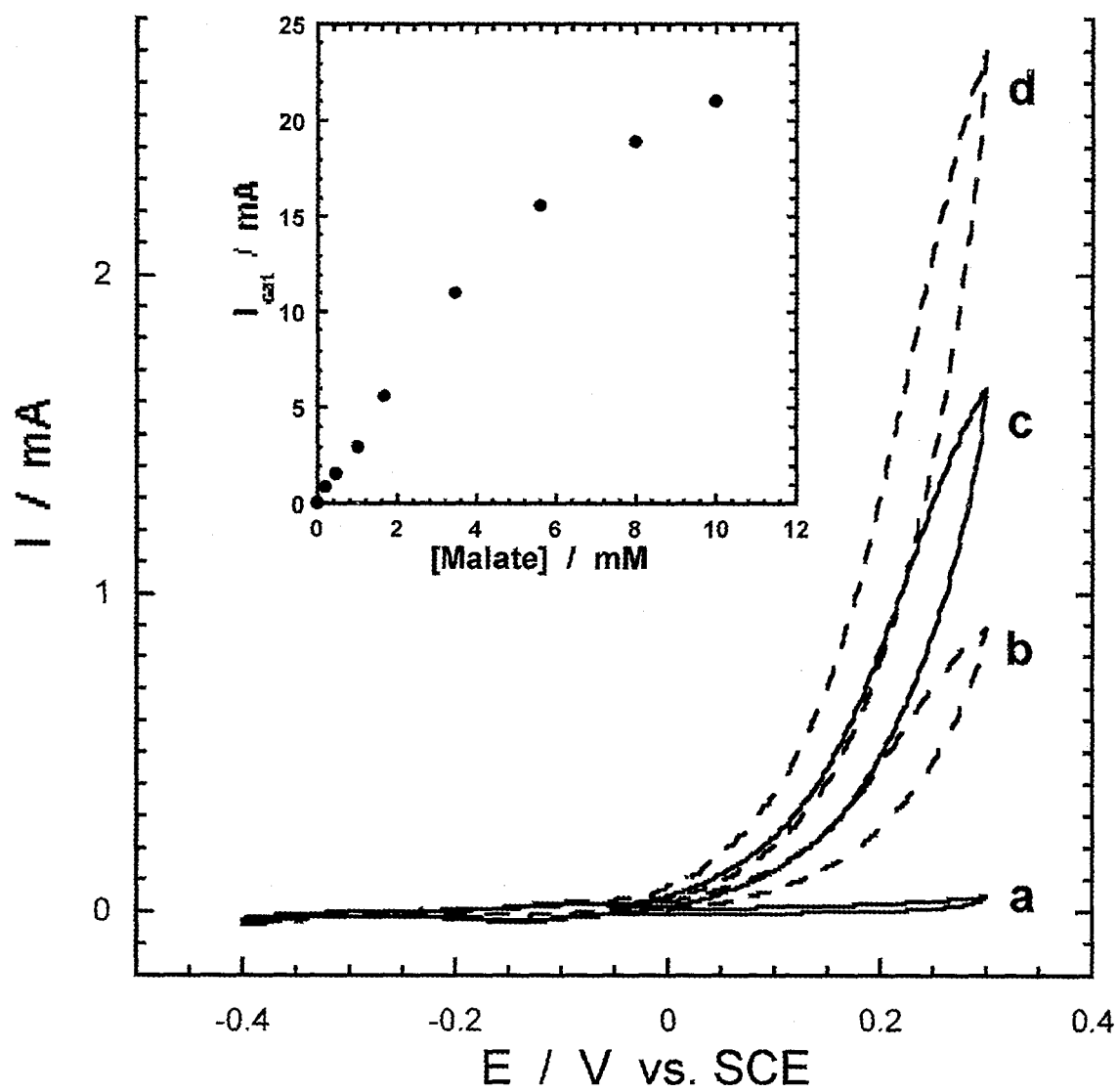
FIG. 7 is a graph showing cyclic voltammograms of the electrode of FIG. 5. Curves a–d show cyclic voltammograms of the enzyme-electrode in the presence of different concentrations of malate: (a) 0 mM, (b) 0.25 mM, (c) 0.5 mM, (d) 1 mM. The cyclic voltammograms were recorded in 0.1 M phosphate buffer, pH 7.0, as a background electrolyte under argon at the potential scan rate 5 mV s$^{-1}$. The inset shows a calibration plot of the amperometric responces (at E=0.3 V vs. SCE) measured with various concentrations of malate.

FIG. 7 shows the bioelectrocatalytic oxidation of malate by the electrode functionalized with PQQ/aminophenylboronic acid/$NADP^+$/malic enzyme (see Scheme 3). Curves a–d show cyclic voltammograms of the enzyme-electrode in the presence of different concentrations of malate: (a) 0 mM, (b) 0.25 mM, (c) 0.5 mM, (d) 1 mM. The cyclic voltammograms were recorded in 0.1 M phosphate buffer, pH 7.0, as a background electrolyte under argon at the potential scan rate 5 mV s$^{-1}$. The inset shows a calibration plot of the amperometric responces (at E=0.3 V vs. SCE) measured with various concentrations of malate.

EXAMPLES

The Electrode Preparations:

Assembling of the Au/Cystamine/PQQ/Aminophenylboronic Acid/FAD/Glucose Oxidase Electrode.

A gold (Au) wire electrode (0.3 cm$^2$ geometrical area, 1.3 roughness factor) was modified with a cystamine monolayer by soaking the electrode in 0.02 M cystamine solution in water for 2 hours; then the electrode was washed with water 5 times. The cystamine-modified electrode was reacted with pyrroloquinoline quinone (PQQ) 1 mM solution in 0.1 M HEPES-buffer, pH 7.3, in the presence of 1-ethyl-3-(3-dimethylaminopropyl)-carbodiimide (EDC), 5 mM, for 2 hours; then the electrode was washed with 0.1 M HEPES-buffer, pH 7.3, two times. The PQQ-functionalized Au-electrode was reacted with aminophenylboronic acid, 1 mM, in 0.1 M HEPES-buffer, pH 7.3, in the presence of EDC, 5 mM, for 2 hours; then the electrode was washed with 0.1 M HEPES-buffer, pH 7.3, two times. The PQQ/aminophenylboronic acid-functionalized Au-electrode was reacted with FAD, 1 mM, in 0.1 M phosphate buffer, pH 7.0, for 2 hours; then the electrode was washed with 0.1 M phosphate buffer, pH 7.0, two times. The FAD-functionalized Au-electrode was interacted with apo-glucose oxidase (apo-GOx), 1 g mL$^{-1}$, in 0.1 M phosphate buffer, pH 7.0, for 5 hours; then the enzyme-reconstituted electrode was washed with 0.1 M phosphate buffer, pH 7.0, two times. This procedure is illustrated in FIG. 1.

Assembling of the Au/Cystamine/PQQ/Aminophenylboronic Acid/$NADP^+$/Malic Enzyme Electrode.

A gold (Au) wire electrode (0.3 cm$^2$ geometrical area, 1.3 roughness factor) was modified with a cystamine monolayer by soaking the electrode in 0.02 M cystamine solution in water for 2 hours; then the electrode was washed with water 5 times. The cystamine-modified electrode was reacted with pyrroloquinoline quinone (PQQ) 1 mM solution in 0.1 M HEPES-buffer, pH 7.3, in the presence of EDC, 5 mM, for 2 hours; then the electrode was washed with 0.1 M HEPES-buffer, pH 7.3, two times. The PQQ-functionalized Au-electrode was reacted with aminophenylboronic acid, 1 mM, in 0.1 M HEPES-buffer, pH 7.3, in the presence of EDC, 5 mM, for 2 hours; then the electrode was washed with 0.1 M HEPES-buffer, pH 7.3, two times. The PQQ/aminophenylboronic acid-functionalized Au-electrode was reacted with $NADP^+$, 1 mM, in 0.1 M phosphate buffer, pH 7.0, for 2 hours; then the electrode was washed with 0.1 M phosphate buffer, pH 7.0, two times. The $NADP^+$-functionalized Au-electrode was interacted with malic enzyme (MalE), 1 g mL$^{-1}$, in 0.1 M phosphate buffer, pH 7.0, for 10 minutes; then the enzyme-electrode was treated with 10% (v/v) glutaric dialdehyde solution in 0.1 M phosphate buffer, pH 7.0, for 10 minutes; then the cross-linked enzyme-electrode washed with 0.1 M phosphate buffer, pH 7.0, two times. This procedure is illustrated in FIG. 5.

Assembling of the Au/Cystamine/PQQ/Aminophenylboronic Acid/$NAD^+$/Lactate Dehydrogenase Electrode.

Figure 6:
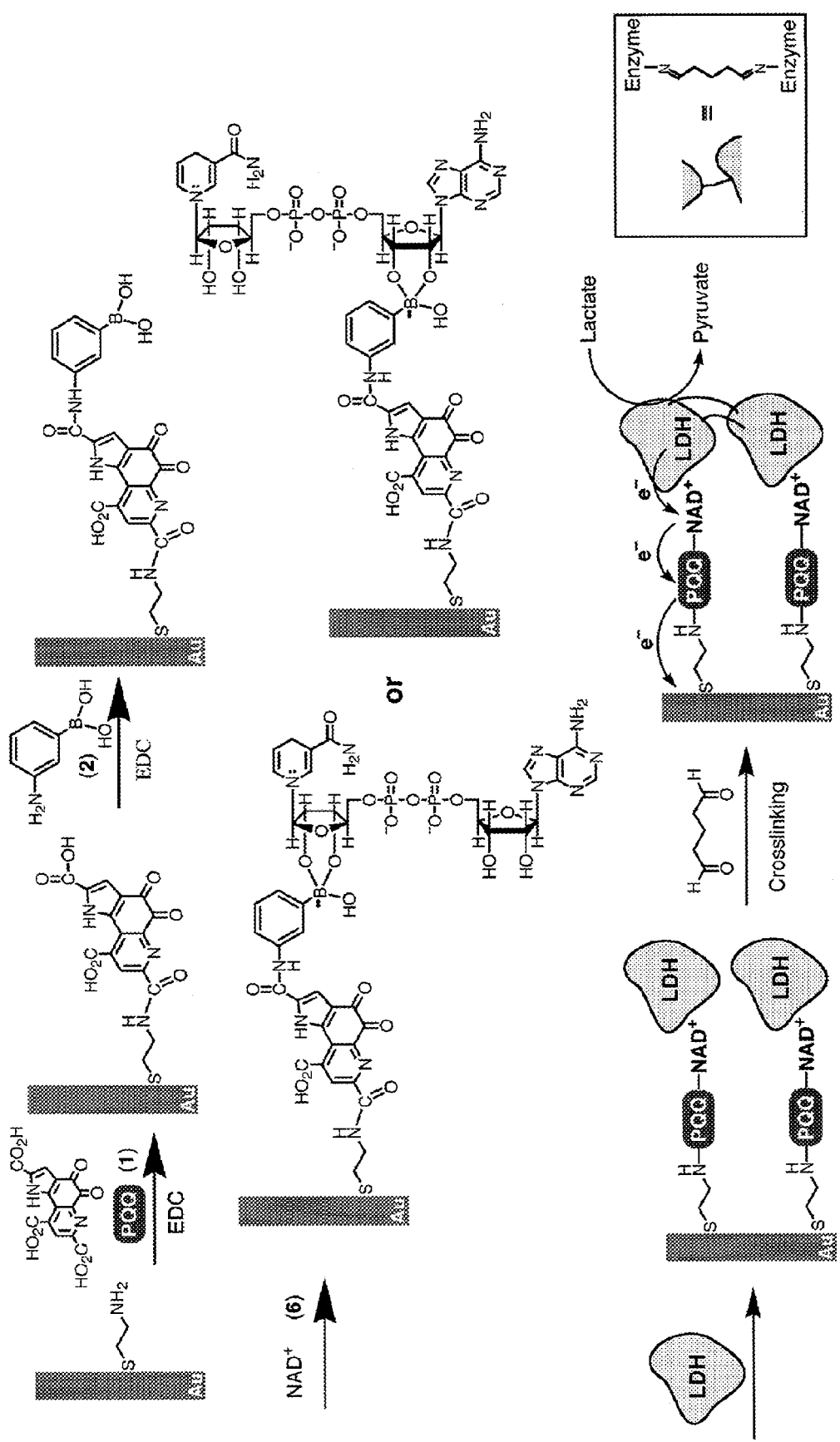
FIG. 6 illustrates the assembly of the reconstituted LDH-electrode and the bioelectrocatalytic oxidation of lactate at this electrode.

A gold (Au) wire electrode (0.3 cm$^2$ geometrical area, 1.3 roughness factor) was modified with a cystamine monolayer by soaking the electrode in 0.02 M cystamine solution in water for 2 hours; then the electrode was washed with water 5 times. The cystamine-modified electrode was reacted with pyrroloquinoline quinone (PQQ) 1 mM solution in 0.1 M HEPES-buffer, pH 7.3, in the presence of EDC, 5 mM, for 2 hours; then the electrode was washed with 0.1 M HEPES-buffer, pH 7.3, two times. The PQQ-functionalized Au-electrode was reacted with aminophenylboronic acid, 1 mM, in 0.1 M HEPES-buffer, pH 7.3, in the presence of EDC, 5 mM, for 2 hours; then the electrode was washed with 0.1 M HEPES-buffer, pH 7.3, two times. The PQQ/aminophenylboronic acid-functionalized Au-electrode was reacted with NAD$^+$, 1 mM, in 0.1 M phosphate buffer, pH 7.0, for 2 hours; then the electrode was washed with 0.1 M phosphate buffer, pH 7.0, two times. The NAD$^+$-functionalized Au-electrode was interacted with lactate dehydrogenase (LDH), 1 g mL$^{-1}$, in 0.1 M phosphate buffer, pH 7.0, for 10 minutes; then the enzyme-electrode was treated with 10% (v/v) glutaric dialdehyde solution in 0.1 M phosphate buffer, pH 7.0, for 10 minutes; then the cross-linked enzyme-electrode washed with 0.1 M phosphate buffer, pH 7.0, two times. This procedure is illustrated in FIG. 6.

The invention claimed is:

1. An electrode carrying immobilized groups having the general formula

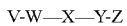

wherein
V is a binding moiety that can chemically associate with, attach to, or chemically sorb onto the electrode;
W is an electron mediator group that can transfer electrons between the electrode an Y;
X is a linker moiety;
Y is a cofactor of a redox enzyme having, when not bound to X, at least one pair of cis hydroxyl groups; and
Z is a redox enzyme;
wherein X is a boronic acid derivative.

2. An electrode according to claim 1, wherein X has the formula

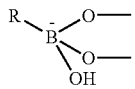

wherein R is an aliphatic or aromatic moiety optionally substituted by at least one carboxy, carbonyl, amino, hydroxy or thio group.

3. An electrode according to claim 1; wherein X is an aminophenyl boronic acid derivative.

4. An electrode according to claim 1, wherein the cofactor is selected from FAD, NAD$^+$ and NADP$^+$.

5. An electrode according to claim 1, wherein the enzyme is selected from glucose oxidase, lactate dehydrogenase and malic enzyme.

6. An electrode according to claim 1 wherein the enzyme is crosslinked using a bifunctional cross-linker capable to react with amino groups, to improve its binding to the electrode.

7. An electrode according to claim 6, wherein said cross-linker is glutaric dialdehyde.

8. A device comprising an electrode according to claim 1.

9. A device according to claim 8, being a biosensor.

10. A biosensor according to claim 9, comprising an electronic circuitry for energizing the electrode and measuring the response.

11. A device according to claim 8, being a fuel cell.

12. A fuel cell according to claim 11, comprising a substrate for the redox enzyme.

13. A process for preparing an electrode carrying immobilized redox enzymes Z comprising:
  (i) forming a layer on the surface of the electrode comprising groups of the formula V-W—X—Y, wherein V is a binding moiety that can chemically associate with, attach to, or chemically sorb onto the electrode and W is an electron mediator group that can transfer electrons between the electrode and Y, Y being a cofactor of the enzyme and X is a linker group;
  (ii) contacting said electrode with one or more enzyme molecule, devoid of a cofactor to complex said enzymes with said cofactor to yield a immobilized groups V-W—X—Y-Z, wherein Z is a catalytically functional enzyme that can catalyze a redox reaction; said method being characterized in that
said cofactor has at least one pair of cis hydroxyl groups and said process comprises binding said cofactor to said electron mediator group by a group X being a boronic acid derivative.

14. A process according to claim 13, wherein X has the formula

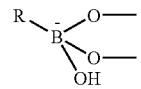

wherein R is an aliphatic or aromatic moiety optionally substituted by at least one carboxy, carbonyl, amino, hydroxy or thio group.

15. A process according to claim 14, wherein R is selected from phenyl, naphthyl and alkyl groups, said groups being optionally substituted by at least one carboxy, carbonyl, amino, hydroxy or thio group.

16. A process according to claim 13, comprising treating said electrode to cross-link the enzyme to a rigid biocatalytic matrix.

17. A process for preparing an electrode carrying immobilized redox enzymes Z comprising:
  (i) forming a layer on the surface of the electrode comprising groups of the formula V-W, wherein V is a binding moiety that can chemically associate with, attach to, or chemically sorb onto the electrode and W is an electron mediator group that can transfer electrons between the electrode and a cofactor Y of the enzyme;
  (ii) binding Y to said groups; and
  (iii) contacting said electrode with one or more enzyme molecule, devoid of a cofactor to complex said enzymes with said cofactor to yield functional enzymes that can catalyze a redox reaction; said method being characterized in that
said cofactor has at least one pair of cis hydroxyl groups and said process comprises binding said cofactor to said electron mediator group by a group X being a boronic acid derivative.

18. A process according to claim 17, wherein (ii) comprises:
  binding a boronic acid or a boronic acid derivative to groups V-W immobilized on the electrode to yield immobilized groups V-W—R—B—(OH)$_2$ and then binding Y to the immobilized groups V-W—R—B—(OH)$_2$ to yield immobilized groups V-W—R—B$^-$(OH)—Y.

19. A process according to claim 17, wherein (ii) comprises:
  binding a group of the formula R—B—(OH)$_2$ to Y to yield a first binding product R—B$^-$(OH)—Y and then binding said first binding product to immobilized groups V-W to yield immobilized groups V-W—R—B$^-$(OH)—Y.

* * * * *